(12) United States Patent
David

(10) Patent No.: US 10,953,730 B2
(45) Date of Patent: Mar. 23, 2021

(54) AIR SCENTING SYSTEM

(71) Applicant: Christopher A. David, Orange, NJ (US)

(72) Inventor: Christopher A. David, Orange, NJ (US)

(*) Notice: Subject to any disclaimer, the term of this patent is extended or adjusted under 35 U.S.C. 154(b) by 125 days.

(21) Appl. No.: 15/342,082

(22) Filed: Nov. 2, 2016

(65) Prior Publication Data
US 2018/0117994 A1   May 3, 2018

(51) Int. Cl.
| A61L 9/14 | (2006.01) |
| B60H 3/00 | (2006.01) |
| B05B 11/00 | (2006.01) |

(52) U.S. Cl.
CPC .............. *B60H 3/0028* (2013.01); *A61L 9/14* (2013.01); *A61L 2209/131* (2013.01); *A61L 2209/15* (2013.01); *A61L 2209/16* (2013.01); *B05B 11/0056* (2013.01); *B05B 11/30* (2013.01); *B60H 2003/0057* (2013.01)

(58) Field of Classification Search
CPC .......... B60H 3/0028; B60H 2003/0057; B60H 2003/0042; B05B 11/30; B05B 11/0056; A61L 9/12; A61L 2209/16; A61L 2209/15; A61L 9/14; A61L 2209/131
See application file for complete search history.

(56) References Cited

U.S. PATENT DOCUMENTS

| 4,549,693 A * | 10/1985 | Barlics | A61L 9/12 206/0.5 |
| 4,570,630 A * | 2/1986 | Elliott | A61M 15/0065 128/203.15 |
| 5,364,027 A | 11/1994 | Kuhn | |
| 5,932,147 A * | 8/1999 | Chen | A61L 9/122 239/56 |
| 6,102,660 A * | 8/2000 | Lee | B60H 3/0028 416/146 R |
| 6,342,003 B1 * | 1/2002 | Wang | B60H 1/345 422/122 |
| 6,610,254 B1 * | 8/2003 | Furner | A01M 1/2033 222/183 |
| 6,685,068 B1 * | 2/2004 | Thompson | A45F 5/00 224/250 |
| 6,772,755 B2 * | 8/2004 | Pera | A61M 15/0028 128/203.12 |
| 6,907,877 B2 * | 6/2005 | Balogh, II | A45F 5/00 128/200.23 |
| 6,976,637 B2 * | 12/2005 | Massimo | A61L 9/12 239/145 |
| 6,983,747 B2 * | 1/2006 | Gallem | A61M 15/0085 128/200.14 |
| 7,140,553 B2 * | 11/2006 | Zobele | A61L 9/12 239/34 |

(Continued)

*Primary Examiner* — Joseph A Greenlund
*Assistant Examiner* — Steven M Cernoch
(74) *Attorney, Agent, or Firm* — Mark Annett

(57) ABSTRACT

The instant devices and approach provide a way to provide custom scented fluids (or air freshener) in the form of evaporated scented air and also atomized scented liquids. It combines a vessel capable of constraining scented fluids or air fresheners with a semipermeable membrane for dispersing evaporated scented air and also an atomizer for dispersing scented liquids into the air and thereby eliminates the need for secondary valves.

13 Claims, 3 Drawing Sheets

(56) References Cited

U.S. PATENT DOCUMENTS

| | | | | |
|---|---|---|---|---|
| 7,350,720 | B2* | 4/2008 | Jaworski | A61L 9/037 239/34 |
| 7,780,094 | B2* | 8/2010 | Caserta | A61L 9/127 239/289 |
| 7,887,759 | B2 | 2/2011 | Triplett | |
| 8,327,842 | B2* | 12/2012 | von Schuckmann | A61M 15/0065 128/203.15 |
| 8,662,480 | B1* | 3/2014 | Irvin | B60H 3/0028 261/26 |
| 8,851,396 | B2* | 10/2014 | Irvin | A61L 9/125 239/326 |
| 9,061,303 | B2* | 6/2015 | Waldner | A61M 15/0085 |
| 2005/0127538 | A1* | 6/2005 | Fabrega | A01M 1/2033 261/104 |
| 2007/0001025 | A1* | 1/2007 | Caserta | A61L 9/127 239/59 |
| 2007/0057084 | A1* | 3/2007 | Vieira | A61L 9/12 239/34 |
| 2007/0237498 | A1* | 10/2007 | Helf | A01M 1/205 392/386 |
| 2009/0143004 | A1* | 6/2009 | Tam | F24F 5/0035 454/284 |
| 2010/0187327 | A1* | 7/2010 | Irvin | A61L 9/125 239/47 |
| 2011/0132992 | A1* | 6/2011 | Hoppe | A61L 9/02 239/6 |
| 2014/0190473 | A1* | 7/2014 | Haindl | A61M 15/009 128/200.23 |
| 2014/0209700 | A1* | 7/2014 | Olchovy | A61L 9/12 239/34 |
| 2016/0228902 | A1* | 8/2016 | Crichton | A61M 35/00 |

* cited by examiner

AIR SCENTING SYSTEM

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

FIELD

The present application relates to systems for dispensing scented fluids.

BACKGROUND

Air fresheners are available in many form factors. In particular, there are automobile air fresheners that come pre-filled with an aromatic liquid that, as the liquid evaporates and becomes a fragrant gas, permeates through a semipermeable membrane.

The problem with these systems is that you are limited to the fragrance supplied by the vendor and they rely solely on evaporation to supply the amount of fragrance in the air, which may or may not be enough. For example, someone eating a fish sandwich in the car may totally overpower the scent emitted by evaporation alone coming from the air freshening device. While it may be possible to use a separate spray air freshener during periods of intense need, it is highly unlikely that they will be emitting the same fragrance and undesirable effects may occur.

Therefore, there continues to be a need for an air scenting system that is fillable by the end consumer and also allows for applying a more intense release of the desired fragrance than is supplied simply do to evaporation.

SUMMARY

In order to overcome the deficiencies in the prior art, systems and methods are described herein.

One aspect of the claimed invention involves an air scenting system comprising a vessel configured to hold an aromatic liquid having at least two apertures. One aperture is configured to be sealed by one or more semi-permeable membranes and the other is configured to be connected to one or more atomizers, whereby both evaporated scented air and atomized scented liquids can be emitted.

Additional aspects involve the end user being able to fill the vessel with a scent of their own choice.

These and other aspects described herein present in the claims result in features and/or can provide advantages over current technology.

The advantages and features described herein are a few of the many advantages and features available from representative embodiments and are presented only to assist in understanding the invention. It should be understood that they are not to be considered limitations on the invention as defined by the claims, or limitations on equivalents to the claims. For instance, some of these advantages or features are mutually exclusive or contradictory, in that they cannot be simultaneously present in a single embodiment. Similarly, some advantages are applicable to one aspect of the invention, and inapplicable to others. Thus, the elaborated features and advantages should not be considered dispositive in determining equivalence. Additional features and advantages of the invention will become apparent in the following description, from the drawings, and from the claims.

DETAILED DESCRIPTION

The instant devices and approach provide a way to provide custom scented fluids (or air freshener) in the form of both evaporated scented air and atomized scented liquids.

FIG. 1A-D show, in simplified form, respectively a front, back, exploded, and a partially assembled view.

Figure 1A:
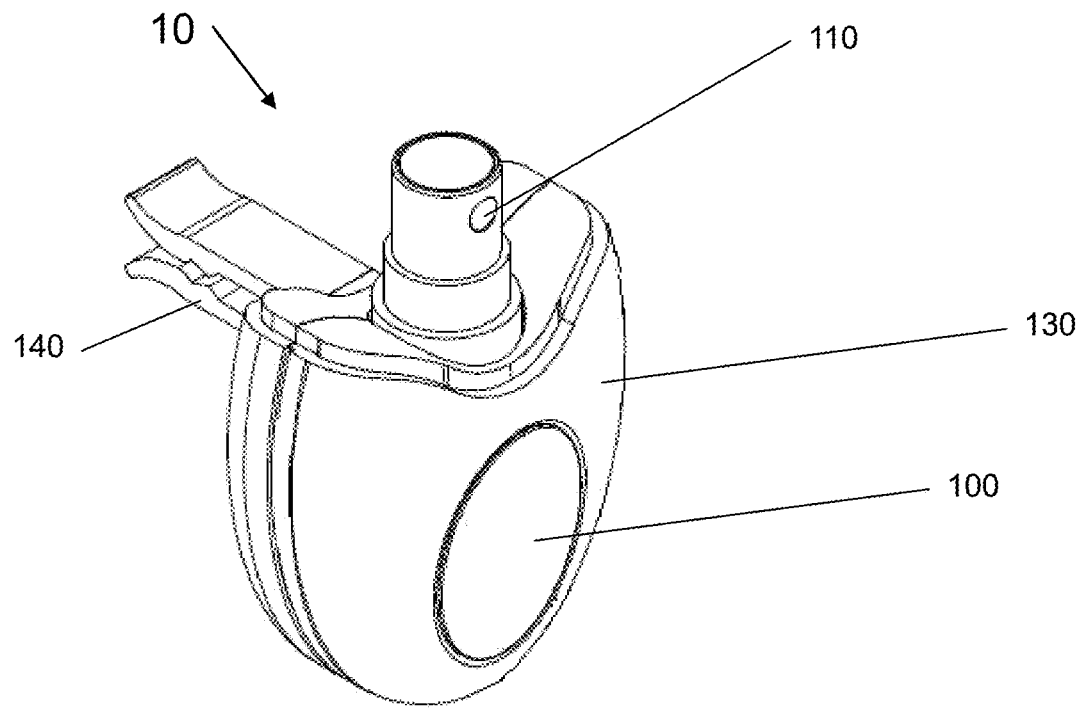
FIG. 1A-D show, in simplified form, respectively a front, back, exploded, and a partially assembled view.
Figure 1B:
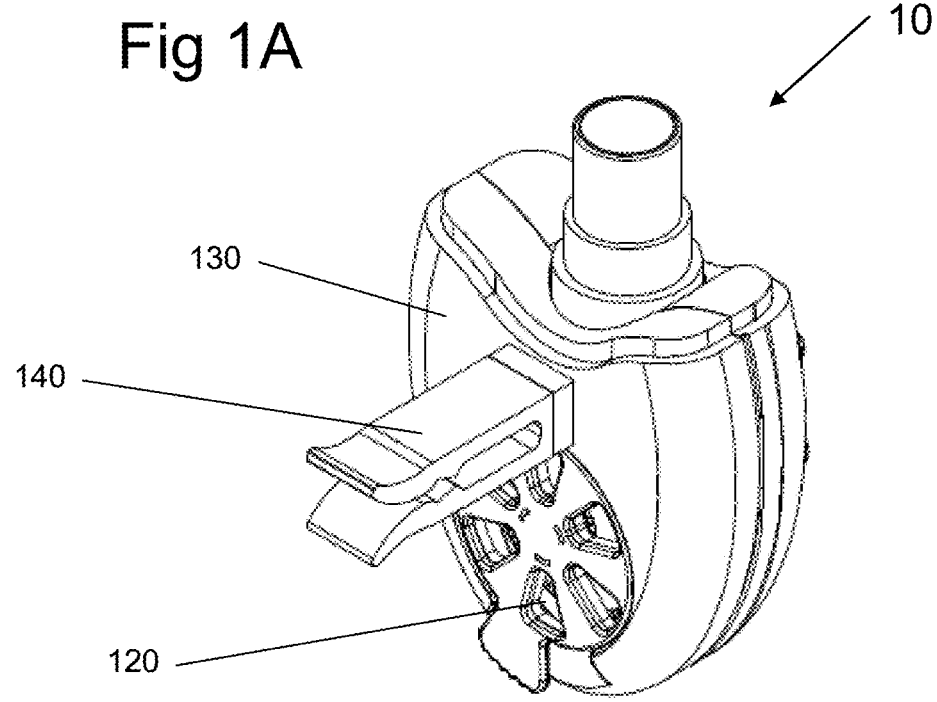

In FIG. 1A-B a representative air scenting system 10 is shown. Atomized scented liquids are stored in vessel 100 and are ejected out of atomizing port 110 and evaporated scented air is emitted out of ports 120. The vessel 100 is shown as encapsulated in cover 130 and attachment 140 is shown as a clip but could be any type of attachment or even a stand for supporting the device on a table or counter.

Figure 1C:
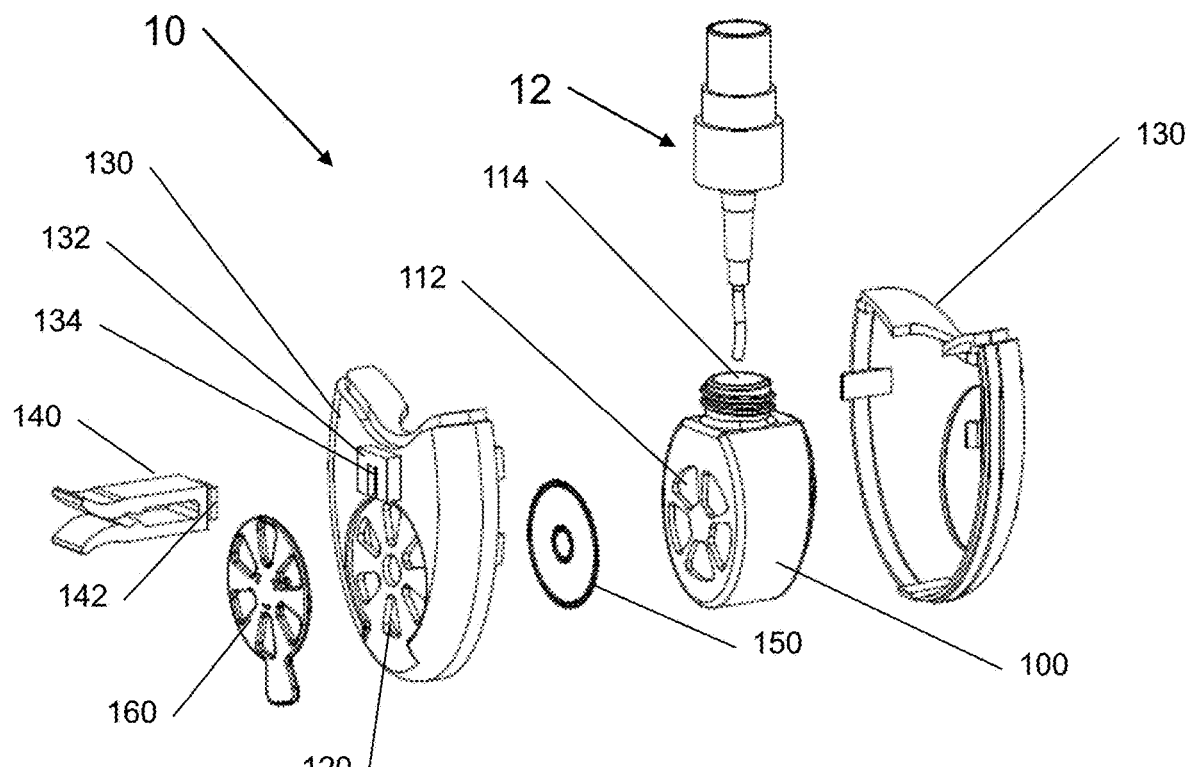
Figure 1D:
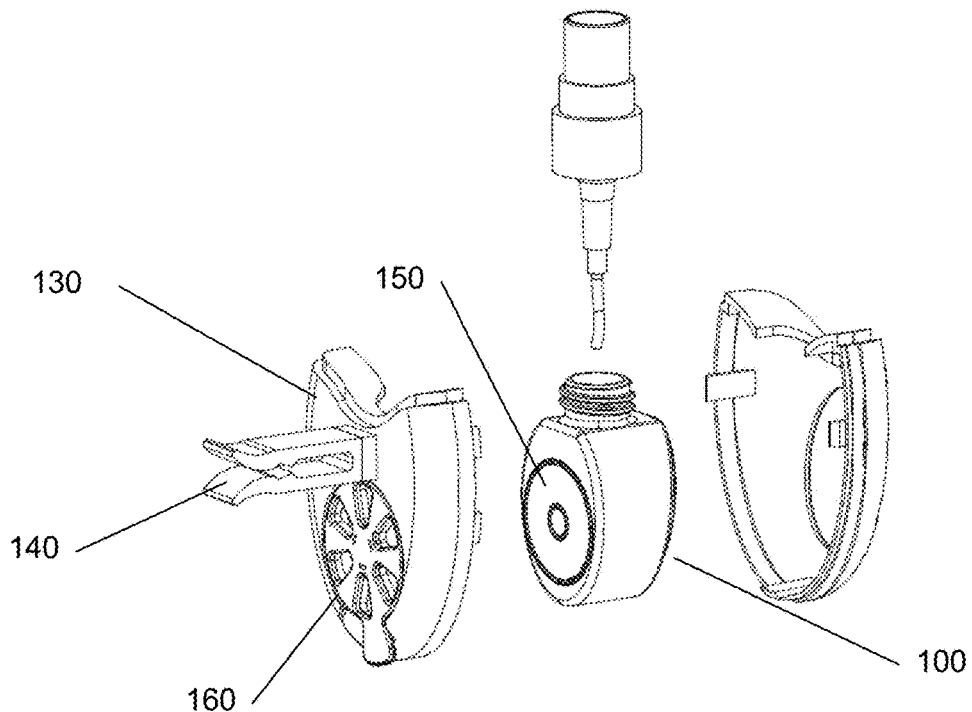

In the exploded and partially assembled views of FIGS. 1C and 1D additional components and features are visible. Vessel 100 is shown as having a plurality of evaporation apertures 112 and one (or more) atomizing apertures 114. One (or more) semipermeable membranes 150 are sealed over the plurality of evaporation apertures 112.

The sealing of the semipermeable membrane 150 over the plurality of evaporation apertures 112 can be accomplished by direct attachment such as adhesive, solvent, thermal (e.g. heat, ultrasonic . . . etc.) bonding or indirectly for example similar to the retaining ring of a Mason® jar where in this instance there could be a membrane cover (not shown) or the cover 130 could be configured to capture the membrane 150 around it's periphery and then seal to the vessel 100. The capturing of the membrane 150 within the membrane cover can be through any of the process mentioned for sealing the membrane 150 to the vessel 100 or it may simply capture it do to compression against the vessel 100.

Whether or not compression is utilized to capture the membrane 150, it is particularly advantageous if the membrane cover (or an appropriately configured cover 130) and the vessel 100 have mating threads (or similar) such that the membrane 150, through the use of the membrane cover, can be removably sealed to the vessel. This is advantageous because it provides a means of the user filling the vessel 100 custom scent. This is also particularly advantageous in the event of compression as it also allows for the capability of disposable membranes 150.

It is worth noting that a refillable semipermeable membrane air scenting system, as disclosed above, regardless of whether or not it is configured to also atomize scented liquids, is a valuable consumer product.

In FIG. 1C additional detail can be seen with regard to attachment 140 and its interconnection to cover 130. In particular, a representative means of attachment can be observed. Cover 130 is shown as having interconnection 132 with a rectangular slot 134. Attachment 140 is shown as having a square mating appendage 142. The square mating appendage 142 is advantageous because it allows the attachment to be oriented at perpendicular orientation (e.g. horizontally or vertically). Other shapes such as a round mating appendage 142 would allow the attachment 140 to be rotated to any angle. Other interconnection between the attachment 140 and the case 13, such as a hinged attachment, allowing the attachment 140 to rotate flat against the case 130 are also anticipated.

Also shown attached to the case 130 is airflow control 160, which is designed to adjust the flow through the evaporation ports 120 and thus regulate the air flowing through the one or more semi-permeable membranes 150. Airflow control 160 is shown as rotatable louver. While a louver is designed to restrict the air flow, other means of increasing air flow, such an a battery operated fan, are also anticipated.

Returning our attention to producing atomized scented liquids, atomizer 12 extends into vessel 110 through atomizing aperture 114 and is shown as pump activated atomizer. While atomizer 12 could be permanently attached to vessel 100, for illustration purposes, atomizer 12 is represented as removably attachable through mating threads (not displayed), which is advantageous in that it allows a different means for the user to add a their own scented fluids to the vessel 100.

Atomizers are well known in the art. However, in order to appreciate an unanticipated benefit of the air scenting systems described here in, it is useful to review the basic operation of an atomizer. To this end, FIG. 2 (Prior Art) shows a representative atomizer.

Figure 2:
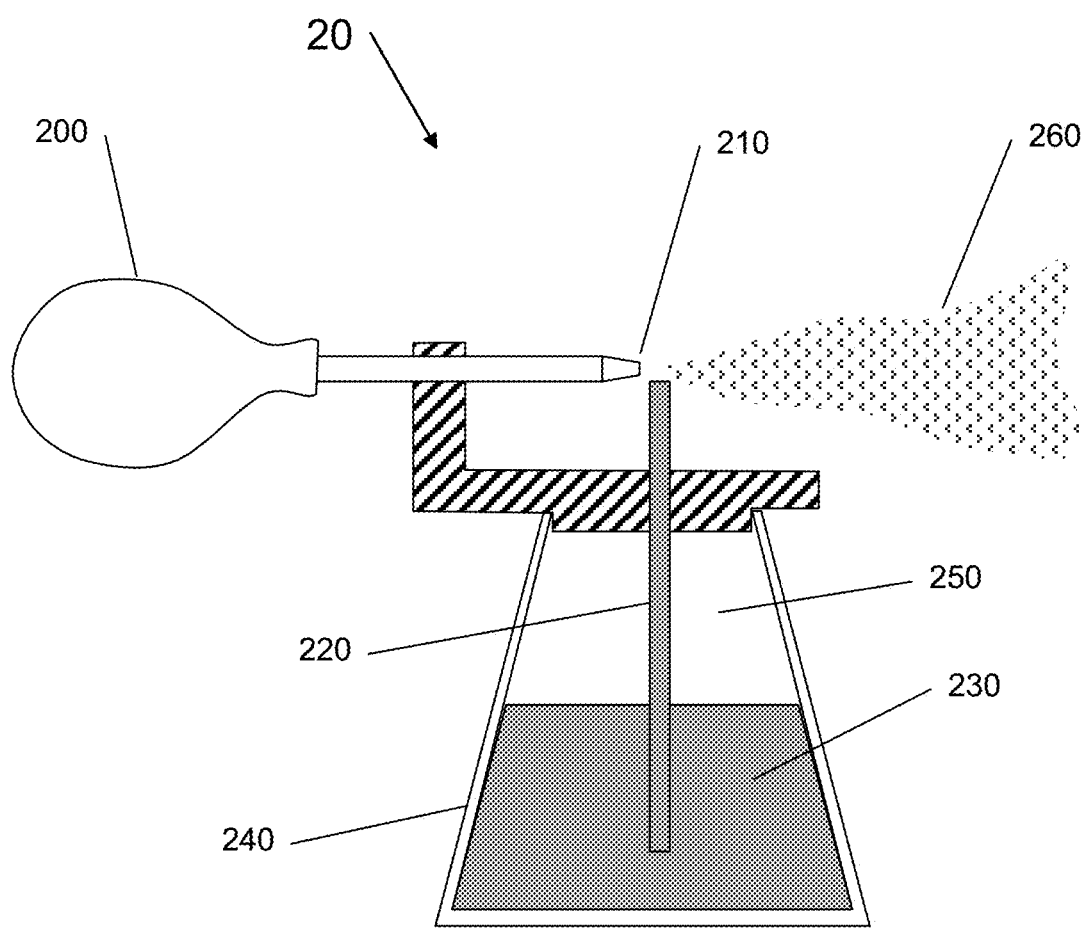
FIG. 2 (Prior Art) shows a representative atomizer.

In FIG. 2 a simplified atomizer 20 is represented. It has a bulb 200 that when squeezed causes air to rapidly flow out port 210 over the top of tube 220. The rapid flow air passed the top of the tube 220 creates a pressure differential (vacuum) between the air 250 above the liquid 230 in the vessel 240 and causes the liquid 230 to be drawn up the tube 220 and become atomized fluid 260 when it mixes with the air flowing out of port 210.

What is not appreciated is that if vessel 240 is sealed then every time liquid 230 is withdrawn then the volume of air 250, above the liquid 230, gets bigger. The increase in air volume causes a drop in air pressure above the liquid and creates a vacuum. If enough liquid 230 is withdrawn then the pressure differential when the bulb 200 is squeezed may not be sufficient to cause atomization.

To overcome this problem, the simplest solution is to put a hole in the vessel 240 above the liquid 230 such that air can freely flow back into the vessel 240. However, this is disadvantageous as anyone that has ever turned an older perfume bottle upside down and had it leak all over his or her hand knows.

To overcome this problem people have gone to elaborate lengths and created complex systems of valves to open and close at just the right point of the atomization cycle. However, an unanticipated benefit of the air scenting systems described herein is that by combining a semipermeable membrane for evaporation that there is no need for a secondary venting system.

Finally, it is to be understood that various different variants of the invention, including representative embodiments and extensions have been presented to assist in understanding the invention. It should be understood that such implementations are not to be considered limitations on either the invention or equivalents except to the extent they are expressly in the claims. It should therefore be understood that, for the convenience of the reader, the above description has only focused on a representative sample of all possible embodiments, a sample that teaches the principles of the invention. The description has not attempted to exhaustively enumerate all possible permutations, combinations or variations of the invention, since others will necessarily arise out of combining aspects of different variants described herein to form new variants, through the use of particular hardware or software, or through specific types of applications in which the invention can be used. That alternate embodiments may not have been presented for a specific portion of the description, or that further undescribed alternate or variant embodiments may be available for a portion of the invention, is not to be considered a disclaimer of those alternate or variant embodiments to the extent they also incorporate the minimum essential aspects of the invention, as claimed in the appended claims, or an equivalent thereof.

What is claimed is:

1. An air scenting system comprising:

a vessel comprising a top, bottom, and a back and configured to hold a stored aromatic liquid and the vessel having at least a first and second apertures wherein at least the first aperture is on the back and is configured to be sealed by one or more semi-permeable membranes and wherein at least second aperture is on the top and configured to be connected to one or more atomizers;

wherein the first and second apertures are configured as separate paths to allow aromatic air via the first aperture and atomized aromatic liquids via the second aperture, from the same stored aromatic liquid, to pass out of the vessel;

one or more semi-permeable membranes configured to only allow evaporated aromatic air to pass through the membrane and to otherwise prevent the aromatic liquids in contact with the one or more semi-permeable membranes from passing through the one or more semi-permeable membranes;

one or more membrane covers, wherein the one or more membrane covers are associated with the sealing of the first aperture and is configured to be connected to the vessel and to seal the one or more semi-permeable membranes when the membrane cover is connected to the vessel and wherein the one or more membrane covers are vented to allow air to pass through the one or more semi-permeable membranes and out of the vessel; and one or more pump activated atomizers configured to be attached to the vessel and to atomize the aromatic liquid within the vessel.

2. The system of claim 1 further comprising an airflow control configured to regulate the air flow passing through the one or more semi-permeable membranes.

3. The system of claim 2 wherein the airflow control is an adjustable louvre system and the adjustable louvre is coincident with the back and extends towards the bottom of the vessel.

4. The system of claim 1 further comprising an attachment mechanism configured to allow the device to be supported by another surface.

5. The system of claim 4 wherein the attachment mechanism is a clip designed to attach to the vent of a car.

6. The system of claim 4 wherein the attachment mechanism is rotatable.

7. The system of claim 1 wherein the one or more semi-permeable membranes are sealed by thermal bonding.

8. The system of claim 1 wherein the membrane cover is configured to be removably connected to the vessel.

9. The system of claim 8 wherein the removable connection is through mating threads associated with both the vessel and the membrane cover.

10. The system of claim 1 wherein the membrane cover is connected by thermal bonding.

11. The system of claim 1 wherein the one or more semi-permeable membranes are sealed by thermal bonding.

12. The system of claim 1 wherein the aromatic liquid is fillable by an end user through the first aperture.

13. The system of claim 1 wherein the aromatic liquid is fillable by an end user through the second aperture.

* * * * *